United States Patent [19]

Hallmark

[11] Patent Number: 4,917,605
[45] Date of Patent: Apr. 17, 1990

[54] DENTAL LOCKING CLASP MEMBER

[76] Inventor: Ralph Hallmark, 80 S. Howell Ave., Centerreach, N.Y. 11720

[21] Appl. No.: 281,666

[22] Filed: Dec. 9, 1988

[51] Int. Cl.⁴ .................................... A61C 13/225
[52] U.S. Cl. .................................................... 433/178
[58] Field of Search ................ 433/178, 179, 6, 18, 433/19, 21

[56] References Cited

U.S. PATENT DOCUMENTS

| | | | |
|---|---|---|---|
| 1,591,155 | 7/1926 | Craigo | 433/178 |
| 1,591,156 | 7/1926 | Craigo | 433/178 |
| 2,118,555 | 5/1938 | Giffen | 433/178 X |
| 2,789,350 | 4/1957 | Fischer | 433/178 X |
| 3,436,825 | 4/1969 | Oddo, Jr. | 433/178 |
| 4,014,094 | 3/1977 | Schumann | 433/178 X |

Primary Examiner—Robert P. Swiatek
Assistant Examiner—Nichols D. Lucchesi
Attorney, Agent, or Firm—William G. Valance

[57] ABSTRACT

The dental locking clasp member comprises a U-shaped piece having twin arms with substantially flat parallel opposing inner surfaces connected to an anchor portion having a plurality of anchor grooves. The twin arms have twin opposing locking recesses adjacent the free ends. Additional auxiliary parts may be part of the locking clasp member and include a bar portion with a curved spur, a receptacle portion which has locking projections which engage in the locking recesses in the case of a labial locking clasp and a clasp stem also with locking projections with a stop in the case of a buccal locking clasp. When the additional auxiliary parts are made of wax the entire locking clasp member may be used with a wax pattern to produce a completed partial casting with the appropriate locking clasp in a single casting operation which does not require reworking.

9 Claims, 2 Drawing Sheets

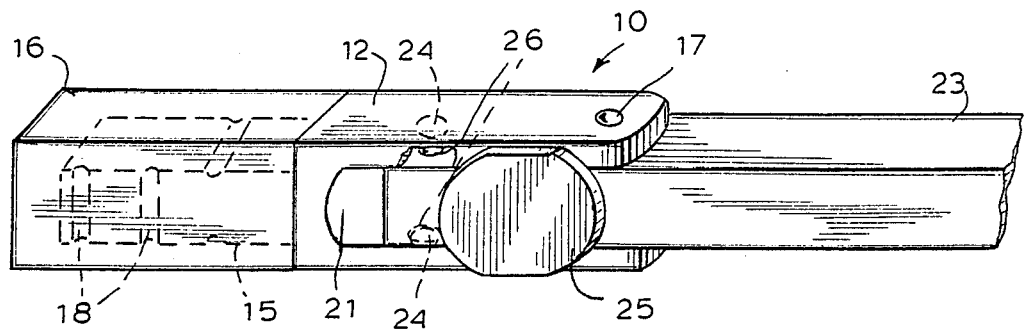
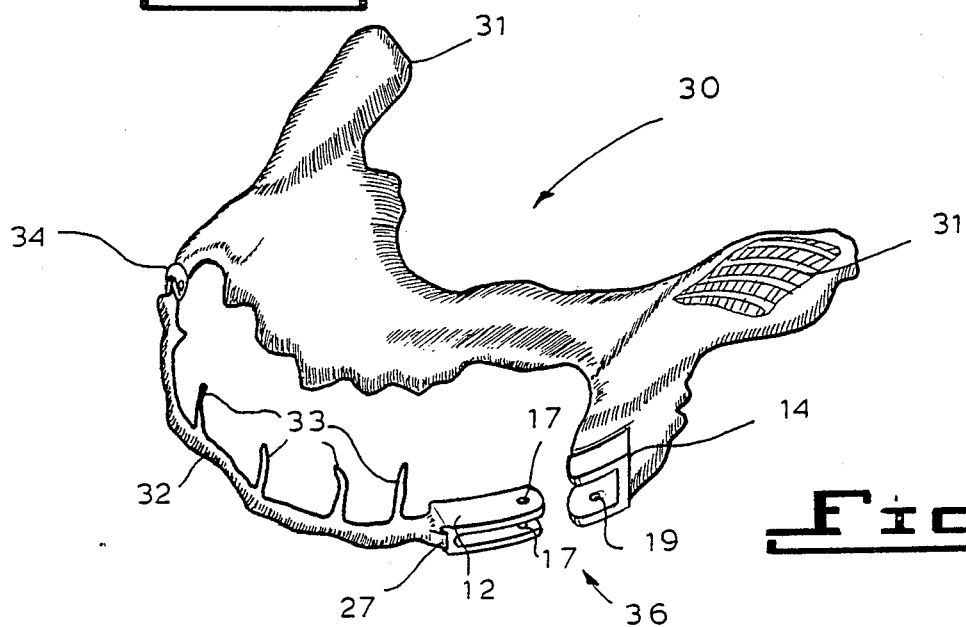
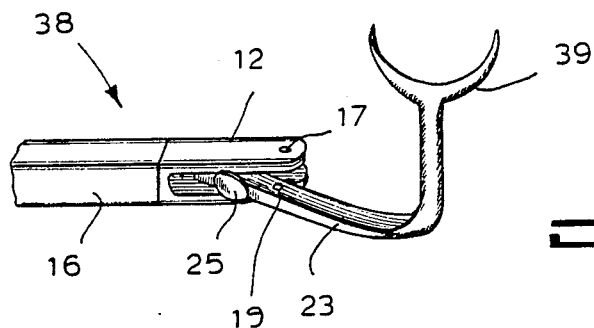

DENTAL LOCKING CLASP MEMBER

THE FIELD OF THE INVENTION

My invention relates to a clasp or a locking means for a dental appliance and, more particularly, to a part, member or piece which is used to make a clasp or locking means for a dental appliance.

THE BACKGROUND OF THE INVENTION

A removable dental appliance which comprises one or more artificial teeth, an acrylic holding means for the artificial teeth and a metal partial casting which acts as a base member for the artificial teeth is well known in dentistry. It is used to replace teeth which have been lost as a result of age or accident. The metal partial casting provides a means of holding the dental appliance securely in the mouth anchoring it on the remaining natural teeth by means of retentive clasping. But conventional clasping does not always supply the required retention. Extraordinary means must then be used. To be removable it must also contain a clasp or locking means. That clasp or locking means and the way that it is made is the concern of the present invention.

Generally the partial casting is made first on a refractory model which supports a partial wax pattern shaped exactly like the metal partial casting. Currently the locking clasp must be incorporated in the partial casting after the main portion of the partial casting has been cast. Thus two or more separate castings are required involving comparatively more time and labor. Also it is difficult to adjust some current locking clasps which are essentially a simple latch which, when they are made, can be misaligned so that they are difficult to open and close. Also some current locking clasps are comparatively weak.

Furthermore current procedures for making a partial casting with a locking clasp require that wax members be positioned in very close proximity to each other, keeping them separated with critical space tolerances necessary to their proper function. Quite often these spaces are bridged due to investment breakdown. This flawed joining of the wax members necessitates that a carbide burr be employed to remove the obstruction so that the two parts of the locking clasp can be separated. Also it is possible for the maker to misjudge the amount or degree of retention needed to have a properly working locking clasp. If there is a misjudgment at this critical step and too much retention results, then the locking clasp can not be opened and a carbide burr must be used to reduce the excess metal. Thus substantial reworking with a carbide burr after casting results in consumption of additional time and money and weakens and defaces the unit.

It is a general object of the instant invention to provide a locking clasp or locking means for a dental appliance which has none of the above-described disadvantages.

It is an object of the present invention to provide a locking clasp member for a locking clasp of a dental appliance, with which the locking clasp can be made with less time and labor than the current locking clasp.

It is also an object of the present invention to provide an improved locking clasp member which can be used to make a locking clasp in a dental appliance which does not require extensive reworking because of inaccurate casting procedures or misjudgments.

It is an additional object of the instant invention to provide an improved locking clasp member which is universally applicable for making a wide variety of comparatively strong dental locking clasps for both buccal and labial regions of the mouth.

It is another object of the present invention to provide an improved locking clasp member which can be used to make a locking clasp in a dental appliance which is more easily adjusted for wear than the current locking means.

It is still another object of the present invention to provide an improved locking clasp member which can make a locking clasp which can be used on a completed partial casting in need of altered or additional clasp retention.

SUMMARY OF THE INVENTION

According to my invention the dental locking clasp member used to make a locking clasp for a dental appliance comprises a U-shaped piece having twin arms with substantially flat parallel opposing a inner surfaces rigidly attached to an anchor portion having a plurality of anchor grooves. Each of the arms has a locking recess adjacent its free end. Each of the locking recesses may be substantially circular and should have a depth sufficient to permit flexing of the arms of the U-shaped piece in any of two directions to permit a locking engagement with locking projections provided on other pieces of the locking clasp member or the locking clasp.

A bar end portion can advantageously be provided surrounding the anchor portion and engaged in the anchor grooves. Furthermore the anchor portion may be directed substantially parallel to the longitudinal direction of the arms. The bar end portion can be provided with a curved spur whose tip is directed substantially parallel to the adjacent outer surface of the bar end portion.

When the dental locking clasp member is used to make a labial locking clasp or labial lock, as it has been called, each arm of the U-shaped piece has another locking recess advantageously provided on the outer surface of the arm adjacent the free end of the arm and the dental locking clasp member further comprises a receptacle portion having two locking projections positioned to engage in these other locking recesses in the outer surfaces of the arms to hold the U-shaped piece fixed in the receptacle portion.

When the dental locking clasp member is used to make a buccal locking clasp or a Roach clasp for a dental appliance, the locking clasp member further comprises a clasp stem having a stop and two locking projections engagable in the locking recesses on the interior surfaces of the arms to hold the clasp stem in place in the arms. Each of the arms has a pivot recess in one of the substantially flat opposing parallel inner surfaces engagable with a pivot projection located on the clasp stem so that the clasp stem pivots in the arms of the U-shaped piece limited by the stop abutting on the edges of the U-shaped piece. The stop can be a comparatively large mass attached to one side of the clasp stem extending perpendicularly in the direction of at least one of the opposing inner surfaces of the arms of the U-shaped piece.

When the locking clasp member is used to make a Roach clasp or a labial lock all pieces other than the U-shaped piece are first made of wax. This embodiment of the locking clasp member is then used directly in the wax pattern for the partial casting to make the partial casting in a single casting process. Reworking or use of a carbide burr to separate parts is not necessary. The locking clasp member of my invention thus saves considerable time and effort in making the dental appliance. Furthermore it is easily adjusted by bending the arms of the U-shaped member. The recesses must of course have a range of depth and the projections must have an appropriate corresponding height so that the arms can flex sufficiently so that the finished locking clasp can be easily opened and closed. If wear loosens the retention of the partial casting with the locking clasp made from the locking clasp member of my invention, adjustment is simple and effective. The ends of the arms of the U-shaped piece need only be squeezed together or somewhat forced apart. The U-shaped piece with anchor portion can be made in quantity with locking recesses on the inner and outer surfaces and pivot recesses as a universal part useful in making many different dental applicances.

DETAILED DESCRIPTION OF THE DRAWINGS FIGURES

FIG. 4 is a perspective view of another embodiment of the invention with different auxiliary means for making a buccal locking clasp.

FIG. 5 is a perspective view of a completed partial casting for use in a dental appliance in which a finished locking clasp made from the locking clasp member of FIG. 1 is incorporated.

FIG. 6 is a cutaway perspective view of another locking clasp for a different partial casting made using the locking clasp member shown in FIG. 4.

DETAILED DESCRIPTION OF THE INVENTION

Figure 1:
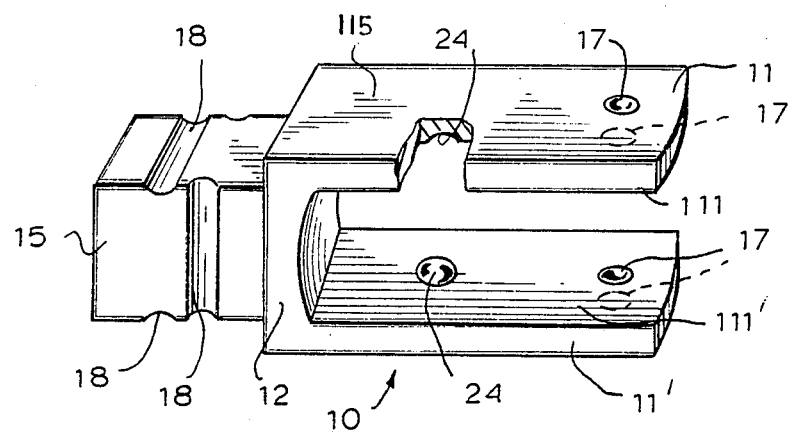
FIG. 1 is a perspective view of a dental locking clasp member according to the invention without auxiliary means for attachment to form a locking clasp.

The dental locking clasp member 10 shown in FIG. 1 is used to make the locking clasp 36 in the partial casting 30 shown in FIG. 5. It comprises a U-shaped piece 12 having twin arms 11,11' with substantially flat parallel opposing inner surfaces 111,111' connected to an anchor portion 15 directed substantially parallel to the longitudinal direction of the arms 11,11'. A locking recess 17 is provided on each of the opposing inner surfaces 111,111' adjacent the free end of each arm 11,11'. A locking recess 17 is also provided on the outer surface 115,115' of each of the arms 11,11' adjacent the free end of the arm 11,11' similar to those recesses 17 placed on the interior guiding surfaces 111,111'. Each locking recess 17 is substantially circular and has a depth sufficient to permit flexing without distortion of the twin arms 11,11' in operation so that the locking clasp made from the locking clasp member 10 may be opened and closed easily but has sufficient retention when closed.

Anchor grooves 18 are provided on the anchor portion 15 which is advantageously shaped like a rectangular cross sectioned bar. These anchor grooves 18 must be deep enough to hold enough metal from the partial casting so that the locking clasp member 10 is held securely in the final partial casting 30.

Figure 2:
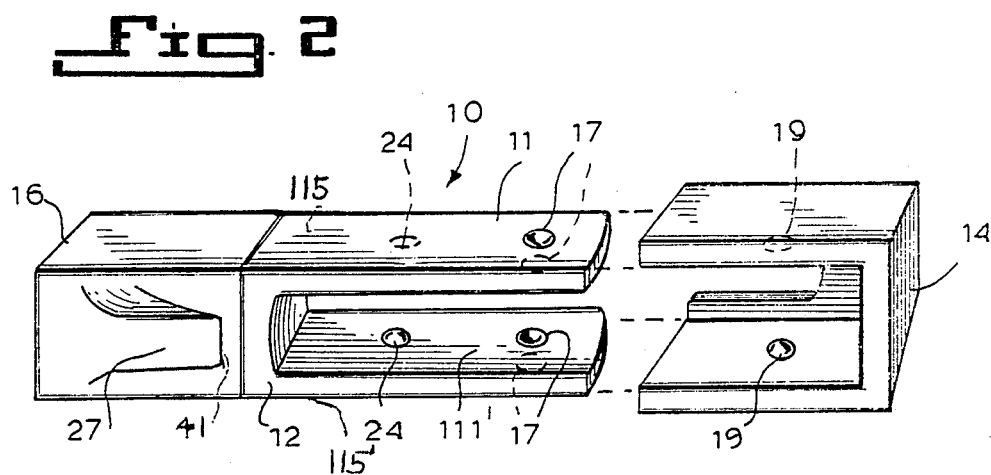
FIG. 2 is a perspective view of the dental locking clasp member of FIG. 1 with auxiliary means for formation of a labial locking clasp.

As shown in FIGS. 2 and 4 depending on which locking clasp 36 or 38 is being made auxiliary attachment means for attachment of the locking clasp member 10 in the final partial casting may be provided. In the embodiment of FIG. 2 these auxiliary attachment means comprise a receptacle portion 14 and a bar end portion 16. In the embodiment shown in FIG. 4 these auxiliary means of attachment comprise a clasp stem 23 with an oval stop 25 and a bar end portion 16.

In the embodiment of FIG. 2 the arms 11,11' of the U-shaped piece 12 may be engaged in a wax receptacle portion 14 which forms the finished metal receptacle portion of the locking clasp 36 in a casting operation. This receptacle portion 14 has flat opposing inner surfaces similar to the inner surfaces 111,111' between which the arms 11,11' of the U-shaped piece 12 are engaged. These flat opposing inner surfaces of the receptacle portion 14 press on the outer surfaces 115,115' of the arms 11,11' and carry locking projections 19 which are positioned to engage in the locking recesses 17.

The receptacle portion 14 is of a length such that the arms 11,11' extend only over a portion of the length of the receptacle portion 14. Thus a space is formed in the freshly cast locking clasp between the arms 11,11' and the facing wall of the receptacle portion 14. A prying tool may be inserted in this space to provide an easy initial separation of the U-shaped piece 12 from the receptacle portion 14 which is especially difficult in current locking clasps. Also retention is particularly easily adjustable.

In the embodiment of FIG. 4 the arms 11,11' of the U-shaped piece 12 hold a wax clasp stem 23 which is of rectangular cross section from which the clasp stem 23 of the locking clasp 38 is made. A wax stop 25 is attached to the wax clasp stem 23. When it contacts the outer edges of the arms 11,11' of the U-shaped piece 12, it limits the pivoting motion of the clasp stem 23 in the arms 11,11' and in the finished locking clasp 38, as well as providing a convenient place to attach a casting sprue. This stop 25 is attached to one side of the clasp stem 23. It is advantageously disk-shaped and extends substantially perpendicular to the opposing inner surfaces of the arms 11,11' and protrudes beyond the side of the clasp stem to which it is attached toward both opposing inner surfaces so that the pivot motion of the clasp stem 23 in the arms 11,11' is limited by the stop 25 abutting on the arms. The clasp stem 23 has pivot projections 26 adjacent the end of the clasp stem 23 in the U-shaped piece 12 on opposite sides facing the parallel opposing inner surfaces 111,111' of the arms 11,11' engaged in the opposing pivot recesses 24 in the inner surfaces 111,111' of the arms 11,11'. Both the pivot recesses and the locking recesses are substantially circular depressions. These pivot recesses 24 are deeper than the locking recesses 17 so that the pivot projections 26 remain engaged in the pivot recesses 24 when the clasp is opened and/or closed. In this embodiment locking recesses 17 are provided on the opposing inner surfaces 111,111' of the arms 11,11' adjacent the free ends of the arms 11,11'. Corresponding locking projections 19 are provided on the clasp stem which engage in the locking recesses similar to the previous embodiment.

One method of making the finished locking clasp 36 or 38 in one casting step is as follows: The auxiliary attachment means including the bar end portion 16 are made of wax. The locking clasp member 10 either with the included wax receptacle portion 14 and bar end portion 16 or the wax bar end portion 16, the clasp stem 23 and stop 25 is connected to a wax pattern prior to casting the partial casting. The wax pattern with the locking clasp member 10 is surrounded by a liquid investment to make the casting mold and then the wax pattern is burned out in a dental furnace. Then hot liquid metal is forced into the mold to form the partial casting with the locking clasp 36 or 38 in a single casting operation.

In the embodiment of FIG. 4 liquid investment 21 is provided between the end of the wax clasp stem 23 and the base of the U-shaped piece 12. Thus when the finished locking clasp 38 shown in FIG. 6 is made the clasp stem 23 may be pivoted from the arms 11,11' on pivot projections 26 to open the locking clasp disengaging the tooth-gripping piece T-clasp 39 from the anchoring tooth, because the liquid investment 21 is removed after casting. When this is done of course the locking projections 19 are disengaged from the locking recesses 17 on the inner facing surfaces 111,111' of the arms 11,11'. The stop 25 prevents the clasp stem 23 from pivoting toward the gums and supplies a convenient place to attach a casting sprue.

Figure 3:
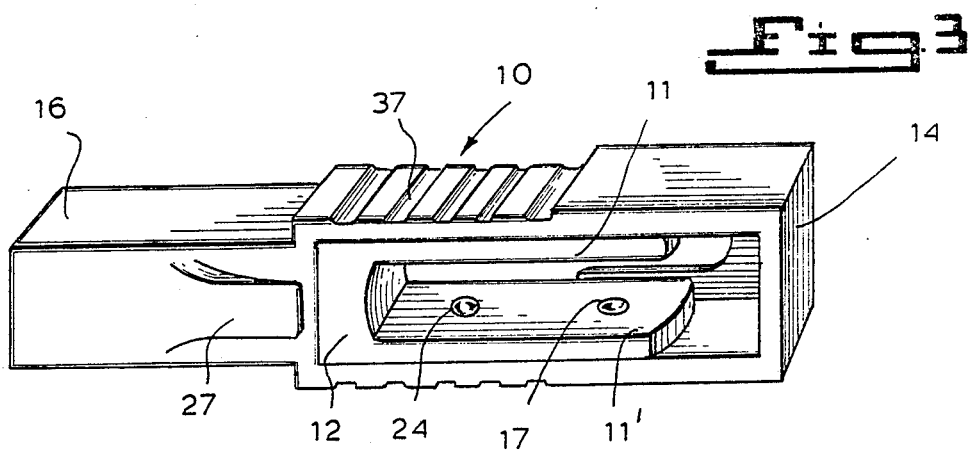
FIG. 3 is a perspective view of the dental locking clasp member of FIG. 1 with additional auxiliary means for making a labial locking clasp.

FIG. 3 shows an additional embodiment in which a serrated supporting section 37 usually of wax is provided connecting the bar end portion 16 and the receptacle portion 14. This feature is usually restricted to the situation where both the bar end portion 16 and the receptacle portion 14 are provided in wax so that the above-described method of making the finished locking clasp easily may be followed. This serrated supporting section 37 retains the two portions 16 and 14 reliably and must be removed before the final casting in which the locking clasp 36 is produced with the completed metal partial casting.

A spur 27 which is a curved pointed protruding piece is provided on the bar end portion 16 with a tip 41 which is substantially parallel to the surface of the bar end portion 16. The purpose of this spur 27 is to provide a means by which a fingernail can engage the locking clasp made from member 10 to provide an outward force to open it.

Although the bar end portion 16, the receptacle portion 14, the clasp stem 23 and the stop 25 are advantageously made of wax in the product as it may be sold, the invention is not limited to an embodiment in which those portions are made of wax and they may be made of metal as is the casting.

By a "substantially circular depression" when referring to a locking or pivot recess in the following claims we mean that a cross section of the recess taken in a plane parallel to one of the opposing inner surfaces of an arm of the U-shaped piece appears to be nearly circular in shape.

LIST OF REFERENCE NUMBERS

10 Dental locking clasp member(the invention)
11,11' arm
12 U-shaped piece
14 receptacle portion
15 anchor portion
16 bar end portion
17 locking recess
18 anchor groove(in anchor portion)
19 locking projection
21 liquid investment
23 clasp stem
24 pivot recess
25 stop
26 pivot projection
27 spur
30 metal partial casting
31,31' saddle portions
32 labial bar
33 retentive prongs
34 labial bar hinge
36 labial bar locking clasp
37 serrated supporting section
38 Roach clasp or buccal locking clasp
39 T-clasp piece
41 tip of spur
111,111' flat opposing inner surfaces (of arms 11,11')
115,115' outer surfaces of arms 11,11'

What is claimed is new and what is desired to be protected by Letters Patent is:

1. A dental locking clasp member used as part of a locking clasp in a partial casting appliance comprising:
   a U-shaped piece having twin arms attached to an anchor portion having a plurality of anchor grooves, each of said arms having a locking recess adjacent a free end of said arm, said locking recesses being substantially circular and having a depth sufficient to permit flexing of said arms of said U-shaped piece in any of two directions to permit locking engagement;
   a bar end portion surrounding said anchor portion and engaged in said anchor grooves, which is provided with a curved spur whose tip is directed substantially parallel to the adjacent outer surface of said bar end portion; and
   a receptacle portion having two locking projections positioned to engage in said locking recesses of said arms to hold said U-shaped piece fixed in said receptacle portion.

2. A dental locking clasp member used as part of a locking clasp in a partial casting appliance comprising a U-shaped piece having twin arms with substantially flat parallel opposing inner surfaces connected to an anchor portion having a plurality of anchor grooves, each of said arms having a locking recess adjacent the free end of said arm on one of said inner surfaces and another of said locking recesses on an outer surface of said arm also adjacent said free end of said arm and a pivot recess adjacent said locking recess on said parallel inner surface of said arm, each of said locking recesses being substantially circular and having a depth sufficient to permit flexing of said arms of said U-shaped piece in any of two directions to permit a locking engagement while said pivot recesses having a sufficient depth to retain and hold a pivot projection during pivoting.

3. A dental locking clasp member used as part of a locking clasp in a partial casting appliance comprising:
   a U-shaped piece having twin arms with substantially flat parallel opposing inner surfaces rigidly attached to an anchor portion having a plurality of anchor grooves, said opposing inner surfaces each having a locking recess adjacent the free end of said arm and a pivot recess positioned interiorly to said locking recess, each of said locking recesses and said pivot recesses consisting of a substantially circular depression in one of said opposing inner surfaces, a bar end portion surrounding said anchor portion and engaged in said anchor grooves, said bar end portion having a cross section which is substantially rectangular and larger than that of said anchor portion, and a clasp stem having two pivot projections located on said clasp stem so as to be engagable in said pivot recesses so that said clasp stem is pivotable in said arms of said U-shaped piece and also having two locking projections shaped to be received in said locking recesses of said arms to hold said clasp stem in place in said arms, said arms having sufficient flexure so that said clasp stem is lockable when said locking projections engage in said locking recesses, said clasp stem also having a stop attached to one side of said clasp stem extending substantially perpendicular to said opposing inner surfaces of said arms and protruding beyond said side of said clasp stem in the direction of at least one of said opposing inner surfaces so that the pivot motion of said clasp stem in said arms is limited by said stop abutting on one of said arms.

4. A dental locking clasp member used as a locking clasp in a dental appliance comprising a U-shaped piece having twin arms with substantially flat parallel opposing inner surfaces and with substantially flat outer surfaces parallelling said inner surfaces, said U-shaped piece being rigidly connected to an anchor portion having a plurality of anchor grooves, each of said arms having a locking recess adjacent the free end of said arm in one of said inner surfaces and another of said locking recesses in one of said outer surfaces adjacent said free end, each of said locking recesses being a substantially circular depression having a depth such that said arms can flex in any of two directions to permit a locking engagement, and a bar end portion structured to surround said anchor portion and engagable in said anchor portion, said anchor portion being directed substantially parallel to the longitudinal direction of said arms.

5. A dental locking clasp member according to claim 4 wherein said bar end portion is made of wax and is provided with a curved spur whose tip is directed substantially parallel to the adjacent outer surface of said bar end portion.

6. A dental locking clasp member according to claim 4 further comprising a receptacle portion having two locking projections positioned to engage in said locking recesses of said arms to hold said U-shaped piece fixed in said receptacle portion, said locking recesses of said arms being provided on the outer surfaces of said arms.

7. A dental locking clasp member according to claim 6 in which said receptacle portion is made of wax.

8. A dental locking clasp member according to claim 4, wherein a pivot recess is provided on each of said inner surfaces interior to said locking recess thereon and further comprising a clasp stem having two pivot projections located on said clasp stem so as to be engagable in said pivot recesses so that said clasp stem is pivotable in said arms of said U-shaped piece and also having two locking projections shaped to be received in said locking recesses of said arms to hold said clasp stem in place in said arms, said arms having sufficient flexure so that said clasp stem is lockable when said locking projections engage in said locking recesses, said clasp stem also having a stop attached to one side of said clasp stem extending substantially perpendicular to said opposing inner surfaces of said arms and protruding beyond said side of said clasp stem in the direction of at least one of said opposing inner surfaces so that the pivot motion of said clasp stem in said arms is limited by said stop abutting on one of said arms.

9. A dental locking clasp member according to claim 8 in which said clasp stem is made of wax.

* * * * *